United States Patent
Dinges et al.

(10) Patent No.: US 11,592,606 B2
(45) Date of Patent: Feb. 28, 2023

(54) POSITIONING DEVICE FOR POSITIONING A LIGHT-CONDUCTING FIBRE IN A CALIBRATION PORT

(71) Applicant: Omicron-Laserage Laserprodukte GmbH, Rodgau-Dudenhofen (DE)

(72) Inventors: Dieter Dinges, Oberursel (DE); Wolfgang Fürstenberg, Johannesberg (DE); Sönke-Nils Baumann, Aschaffenburg (DE)

(73) Assignee: Omicron-Laserage Laserprodukte GmbH, Rodgau-Dudenhofen (DE)

( * ) Notice: Subject to any disclaimer, the term of this patent is extended or adjusted under 35 U.S.C. 154(b) by 549 days.

(21) Appl. No.: 16/619,610

(22) PCT Filed: Apr. 18, 2018

(86) PCT No.: PCT/EP2018/059877
§ 371 (c)(1),
(2) Date: Dec. 5, 2019

(87) PCT Pub. No.: WO2018/224210
PCT Pub. Date: Dec. 13, 2018

(65) Prior Publication Data
US 2020/0158965 A1 May 21, 2020

(30) Foreign Application Priority Data
Jun. 7, 2017 (DE) ............. 10 2017 112 482.9

(51) Int. Cl.
*F21V 8/00* (2006.01)
*A61N 5/067* (2006.01)
(Continued)

(52) U.S. Cl.
CPC ............. *G02B 6/001* (2013.01); *A61N 5/067* (2021.08); *A61B 2017/00057* (2013.01);
(Continued)

(58) Field of Classification Search
None
See application file for complete search history.

(56) References Cited

U.S. PATENT DOCUMENTS 5,409,483 A * 4/1995 Campbell ............ A61N 5/0601
606/15
5,798,518 A 8/1998 Coleman et al.
(Continued)

FOREIGN PATENT DOCUMENTS

CN 202013442 U 10/2011
CN 204989549 U 1/2016
(Continued)

OTHER PUBLICATIONS

Chinese National Intellectual Property Administration, First Notification of Office Action for Chinese Application No. 1201880037786.0, dated Mar. 12, 2021.
(Continued)

*Primary Examiner* — Jerry Rahll
(74) *Attorney, Agent, or Firm* — SoCal IP Law Group LLP; Guy Cumberbatch

(57) ABSTRACT

The invention relates to a positioning apparatus (100) for positioning a light-guiding fiber (206) in a calibration port (208) of a medical apparatus (202) comprising at least one light source (204) for the light-guiding fiber (206), wherein the positioning apparatus (100) comprises an elongate body (102) with two end faces (110, 112) and at least one side face (116). A channel (104) for receiving the light-guiding fiber (206) is formed in the body (102), said channel extending along a longitudinal axis of the body (102) proceeding from a first end face (110). Here, according to the invention, provision is made for the body (102), at least in one portion, to consist of an opaque material in the region of the channel (104) and/or to be coated with an opaque material and for said body to have at least one cutout (113, 118), which
(Continued)

extends from a side face (116) and/or the second end face (112) of the body (102) to the channel (104) such that radiation emitted by the light-guiding fiber (206) can only emerge from the positioning apparatus (100) in unimpeded fashion through the at least one cutout (113, 118).

20 Claims, 4 Drawing Sheets

(51) Int. Cl.
    *A61N 5/06*       (2006.01)
    *A61B 17/00*     (2006.01)
    *G02B 6/42*       (2006.01)

(52) U.S. Cl.
    CPC ........ *A61N 5/062* (2013.01); *A61N 2005/063* (2013.01); *G02B 6/423* (2013.01)

(56) References Cited

U.S. PATENT DOCUMENTS

| | | | |
|---|---|---|---|
| 6,018,606 A | | 1/2000 | Sogabe et al. |
| 6,282,349 B1 | | 8/2001 | Griffin |
| 6,447,537 B1 | | 9/2002 | Hartman |
| 2007/0041685 A1 | | 2/2007 | Kondo |
| 2009/0287198 A1* | | 11/2009 | Hanley ................. A61B 18/24 606/15 |
| 2015/0011985 A1* | | 1/2015 | Peng ...................... A61B 18/24 606/15 |
| 2016/0367320 A1 | | 12/2016 | Peng et al. |

FOREIGN PATENT DOCUMENTS

| | | |
|---|---|---|
| DE | 90 13 085 U1 | 11/1990 |
| DE | 9013085 U1 | 11/1990 |
| DE | 10 2005 017798 A1 | 11/2006 |
| DE | 10 2006 039 471 B3 | 3/2008 |
| DE | 102006039471 B3 | 3/2008 |
| DE | 10 2014 222738 A1 | 5/2016 |
| DE | 102014222738 A1 | 5/2016 |
| EP | 1714620 B1 | 9/2016 |
| JP | 05-95961 A | 4/1993 |
| JP | 06-047056 A | 2/1994 |
| JP | H10-148734 A | 6/1998 |
| JP | 2013-085737 A | 5/2013 |
| JP | 2015-526177 A | 9/2015 |
| WO | 2018/224210 A1 | 12/2018 |

OTHER PUBLICATIONS

European Patent Office, International Search Report and Written Opinion for PCT Application No. PCT/EP2018/059877, dated Jun. 6, 2018. 22 pages.
German Patent Office, Office Action for Application No. 10 2017 112 482.9, dated Feb. 23, 2018. 8 pages.
Japan Patent Office, Notice of Reasons for Rejection for Japanese Patent Application No. 2019-566588, dated Feb. 22, 2022.
Russian Patent Office, Office Action and Search Report for Russian Application No. 2019136995, dated Jul. 22, 2021.

* cited by examiner

POSITIONING DEVICE FOR POSITIONING A LIGHT-CONDUCTING FIBRE IN A CALIBRATION PORT

RELATED APPLICATION INFORMATION

This patent claims priority from International PCT Patent Application No. PCT/EP2018/059877, filed Apr. 18, 2018 entitled, "POSITIONING DEVICE FOR POSITIONING A LIGHT-CONDUCTING FIBRE IN A CALIBRATION PORT", which claims priority to German Patent Application No. 10 2017 112 482.9, filed Jun. 7, 2017 all of which are incorporated herein by reference in their entirety.

FIELD OF THE INVENTION

The invention relates to a positioning apparatus for positioning a light-guiding fiber in a calibration port of a medical apparatus, a system with a positioning apparatus, at least one light source, and at least one light-guiding fiber, and a method for the use of the same.

BACKGROUND OF THE INVENTION

Multifaceted variants of the use of laser radiation in medical technology are known. In addition to the better-known applications, such as, e.g., surgery or ophthalmology, the coherent monochromatic radiation of a laser source is increasingly also used in conjunction with corresponding medicaments that are activatable by electromagnetic radiation. A prominent example in this respect is photodynamic therapy (PDT).

A patient is administered a medicament within the scope of PDT, said medicament predominantly accumulating on tumor cells or bacteria. The medicament is activated by the absorption of electromagnetic radiation at a certain wavelength, said activation leading to the medicament developing a medicinal effect on the cells on which it has accumulated. By way of example, this allows tumors to be fought or regions of the human body afflicted by certain bacteria to be made visible.

In order to apply electromagnetic radiation or laser radiation to corresponding regions of the human body, the prior art has disclosed the practice of coupling corresponding laser radiation into a light-guiding fiber and output coupling said laser radiation from the light-guiding fiber at the location of the treatment in such a way that the region to be treated is impinged by the radiant flux guided through the fiber to the treatment region. Here, it is necessary to always ensure that the treated regions are impinged at a certain radiance of the laser radiation because an effective treatment is otherwise not possible. By way of example, if the introduced radiance is too low, the medicament is not activated, while a radiance that is too high risks injury of the irradiated tissue.

To this end, the prior art has disclosed a check prior to the start of a treatment, the radiant flux output coupled from a light-guiding fiber at a given input power coupled into the fiber being checked within the scope thereof. By way of example, to this end, the light-guiding fiber can be introduced into an integrating sphere such that the radiant flux radiated by the fiber overall can be detected. Since the fiber should subsequently be used for a medical treatment, and possibly an invasive treatment, it is necessary here to ensure that the medically required sterility of the light-guiding fiber is maintained, even during such a calibration process. To this end, the prior art has disclosed the practice of surrounding the light-guiding fiber with a sterile glass sleeve, which acts as a barrier between the sterile fiber and the non-sterile measuring device for ascertaining the power output coupled from the fiber and which positions the sterile fiber in a measuring device.

The methods known from the prior art for calibrating a laser source always have the problem that it is only the total radiant flux output coupled from the fiber that is ascertained, and not the radiance relevant to a treatment. Here, in the case of a certain radiant flux output coupled from a fiber overall, the radiance output coupled from the fiber may differ in different fiber types. However, this circumstance is not reproduced by the methods known from the prior art, in which only the total radiant flux output coupled from a fiber is detected. Consequently, the risk of an incorrect treatment for a patient on account of a wrong radiance continues to exist even after a correct calibration of a fiber to a desired output coupled radiant flux.

SUMMARY OF THE INVENTION

By contrast, the present invention is based on the object of providing an improved positioning apparatus for positioning a light-guiding fiber in a calibration port, said positioning apparatus allowing a dedicated ascertainment of the radiance emitted by a fiber.

This object is achieved by the positioning apparatus as claimed in the characterizing part of claim 1 and by the system as claimed in claim 17 and the method as claimed in claim 18. Advantageous configurations of the respectively claimed subject matter are specified in claims 2 to 16.

In a first aspect, the invention relates to a positioning apparatus for positioning a light-guiding fiber in a calibration port of a medical apparatus comprising at least one light source for the light-guiding fiber. The positioning apparatus comprises an elongate body with two end faces and at least one side face, wherein a channel for receiving the light-guiding fiber is formed in the body, said channel extending along a longitudinal axis of the body proceeding from a first end face. Here, according to the invention, provision is made for the body, at least in one portion, to consist of an opaque material in the region of the channel and/or to be coated with an opaque material and for said body to have at least one cutout, which extends from a side face and/or the second end face of the body to the channel such that radiation emitted by the light-guiding fiber can only emerge from the positioning apparatus in unimpeded fashion through the at least one cutout.

Here, an "opaque" material should be understood to mean a material that is not transparent to the radiation guided in the light-guiding fiber but rather has a defined absorption or scattering of the radiation output coupled from the light-guiding fiber. Thus, the opaque material brings about a significant attenuation of radiation passing through the material but need not necessarily completely absorb the latter. Here, denoting the material as "opaque" should be understood to mean "not transparent to the radiation output coupled from the fiber".

Here, the configuration of the positioning apparatus according to the invention is advantageous in that, as a result of arranging the at least one cutout in the positioning apparatus, the properties of the positioning apparatus can be adapted to the emission characteristic of a light-guiding fiber guided in the positioning apparatus. This allows the radiance emitted by the light-guiding fiber to be ascertained from the emission characteristic of the light-guiding fiber using an appropriate configuration of the calibration port. By way of example, this is possible should the area of the light-guiding fiber exposed by the cutout be known. If the radiant flux emerging from the positioning apparatus is then measured, this allows the radiance emerging from the light-guiding fiber to be deduced. In this way, an incorrect treatment of a patient on account of a wrong choice of a fiber for a given radiant flux coupled into the fiber, and the wrong intensity output coupled from the fiber connected therewith, can be avoided when the positioning apparatus according to the invention is used with an appropriate calibration process.

Here, the light source of the medical apparatus is preferably a laser source, such as for example one or more laser diodes. Here, the laser diodes can be connected to the light-guiding fiber by way of an appropriate optical unit such that the radiant flux or laser radiation output coupled by the laser diode is coupled into the light-guiding fiber. By way of example, an optical fiber with a thickness of 400-600 µm can be used as a light-guiding fiber. Here, typical radiant fluxes used in the field of PDT lie in the range of 1.5-5 watt.

When choosing the opacity of the material of the positioning apparatus that determines the emission characteristic of the positioning apparatus, care should preferably be taken that the laser radiation output coupled from the light-guiding fiber is absorbed in the positioning apparatus over a defined penetration depth. Otherwise, there would be a risk of damage to the positioning apparatus on account of the radiant flux output coupled from the light-guiding fiber.

In the case of a light-guiding fiber for a medical application, there are substantially two options in respect of the direction in which electromagnetic radiation guided by the light-guiding fiber can be output coupled from the fiber. The guided radiant flux is either output coupled in the axial direction of the fiber or in the radial direction of the fiber.

For the case mentioned second, in which a light-guiding fiber output couples electromagnetic radiation in the radial direction of the fiber, provision is made according to one embodiment for the body of the positioning apparatus to have at least one elongate, lateral cutout, wherein the lateral cutout extends over the length of a part of the channel in the longitudinal direction of the body and extends from the side face of the body to the channel in the radial direction.

Such a positioning apparatus is advantageous in that the emission characteristic of a radially emitting fiber can be ascertained with the aid of the positioning apparatus. Here, with knowledge of the area of the light-guiding fiber exposed by the cutout, the radiance output coupled from the light-guiding fiber can be deduced from the radiant flux emerging from the positioning apparatus.

Here, in a preferred embodiment, at least two elongate, lateral cutouts are provided at the body, said lateral cutouts preferably being disposed level in the longitudinal direction of the positioning apparatus. The use of two cutouts facilitates a better ascertainment of the radiance output coupled from the light-guiding fiber.

In order to avoid the radiation emerging from the cutouts superposing and consequently falsifying an ascertainment of the emerging radiant flux when use is made of two lateral cutouts, provision is made in a preferred embodiment for the body to have at least two elongate, lateral cutouts, said lateral cutouts being respectively disposed pair-by-pair on opposite sides of the channel. In this way, there is a minimum superposition of the radiant flux emerging from the cutouts.

According to a further embodiment, provision is made for the cross section of the lateral cutout to increase from the channel to the side face of the body. Effectively, this yields a funnel-shaped configuration of the lateral cutout. This funnel-shaped configuration is advantageous in that the generally divergent radiation, which is output coupled from the light-guiding fiber, is not impeded during the propagation thereof by the positioning apparatus or by the opaque material of the positioning apparatus in the region of the channel. Consequently, a funnel-shaped configuration of the cutout improves the accuracy of an ascertainment of the radiance output coupled from the light-guiding fiber. If, in the process, a radially emitting light-guiding fiber is not correctly disposed in the positioning apparatus such that the radially emitting region is not disposed below a lateral cutout in full, this becomes noticeable by way of a reduced radiant flux emerging from the positioning apparatus. Consequently, the correct position and orientation of the fiber in the positioning apparatus can easily be identified on the basis of the radiant flux emerging from the positioning apparatus.

In order to ensure that the light-guiding fiber is correctly inserted into the positioning apparatus, provision is made according to a further embodiment for the channel not to penetrate the second end face of the body. Consequently, at its longitudinal end, the channel forms a stop for the light-guiding fiber such that the latter can be correctly positioned more easily. Here, what can be ensured by the choice of the position of the stop relative to the lateral cutout or cutouts is that the light-guiding fiber or the radially emitting region of the fiber is disposed exactly below the lateral cutout of the body of the positioning apparatus. This can avoid part of the fiber inadvertently being covered by the body of the positioning apparatus in the longitudinal direction of the fiber.

Here, the channel preferably extends beyond the length of the cutout in the longitudinal direction of the body. As a result, the fiber is guided again in the longitudinal direction of the positioning apparatus downstream of the cutout in the body of the positioning apparatus, and so said fiber does not jump out of the channel in the region of the cutout during the insertion into the channel of the positioning apparatus. Here, according to a further embodiment, the light-guiding fiber can also be prevented from jumping out of the channel in the region of the lateral cutouts by virtue of the diameter of the cutout in the circumferential direction of the channel being chosen to be smaller than the diameter of the fiber.

In order to facilitate the use of the positioning apparatus with a frontally emitting light-guiding fiber, provision is made according to an alternative embodiment for the body of the positioning apparatus to have a frontal cutout on the second end face of the body, wherein the minimum diameter of the frontal cutout is smaller than the diameter of the light-guiding fiber. This ensures that the radiant flux output coupled from the fiber in the frontal direction can emerge from the positioning apparatus while, at the same time, it is ensured that a light-guiding fiber inserted into the positioning apparatus does not slip out of the channel in the longitudinal direction of the positioning apparatus via the second end face. Here, the minimum diameter of the frontal cutout is preferably chosen in such a way that the fiber in the positioning apparatus is only supported at the cladding of the fiber, while the radiation-guiding core of the fiber is completely exposed by the cutout in the longitudinal direction. Here, the form of the cutout can be adapted to the cross-sectional form of the light-guiding fiber. Usually, such light-guiding fibers have a round cross-sectional form.

In order also to facilitate the use of the positioning apparatus with a frontally emitting light-guiding fiber without cladding in its end region, provision can be made here for a sleeve to be placed onto the end of the fiber before the cladding-free fiber is inserted into the positioning apparatus. When the fiber is then inserted into the positioning apparatus, the sleeve can be supported at the stop formed by the positioning apparatus while the sleeve can be supported, yet again, at corresponding stop elements of the fiber.

In order to ensure an unimpeded propagation of the laser power output coupled frontally from the light-guiding fiber through the frontal aperture, provision is made according to a preferred embodiment for the diameter of the frontal cutout to increase in the direction of the second end face of the body. Thus, a funnel-shaped configuration of the cutout also arises in this case. Here, in the case of the frontally emitting light-guiding fiber, the funnel-shaped configuration of the cutout further is advantageous in that, in the case of a fiber not being introduced in full into the positioning apparatus, the radiant flux emerging from the cutout is significantly reduced in relation to the case where the fiber has been introduced in full. Consequently, a measurement of the radiant flux emerging from the positioning apparatus allows ascertainment as to whether a fiber was inserted correctly, i.e., in full, into the positioning apparatus.

In order to simplify the production and handling of the positioning apparatus according to the invention, provision is made according to one embodiment for the surface of the body to be rotationally symmetric about the longitudinal axis of the body, wherein the at least one side face of the body is a lateral face of the solid of revolution. In this case, the positioning apparatus may be produced as a body of revolution for example and generally is more easily usable in a correspondingly shaped calibration port on account of the round form.

Here, the solid of revolution of the positioning apparatus according to a further embodiment has at least two portions in the longitudinal direction, wherein a first portion, which extends from the first end face, has a greater radius than the remaining portions. In this way, the first portion serves as a stop that limits the insertion of the positioning apparatus into a calibration port of a medical apparatus. This simplifies clean and exact positioning of the positioning apparatus in the calibration port.

According to a further embodiment, the correct positioning of the positioning apparatus in a calibration port is also simplified by virtue of the positioning apparatus comprising at least one alignment element, the latter being embodied to set the alignment of the positioning apparatus in the calibration port. This is advantageous, particularly in the case of a rotationally symmetric body of the positioning apparatus. By way of example, the alignment element can be a longitudinal tongue that engages in a corresponding groove of a calibration port upon insertion of the positioning apparatus in the calibration port such that a rotation of the body of the positioning apparatus in the calibration port is prevented. Particularly when using a positioning apparatus with lateral cutouts, this always guarantees that the lateral cutouts are correctly aligned with respect to corresponding detection elements of the calibration port.

In addition to the above-described variant in which the alignment element is embodied as a longitudinal tongue, the alignment element is alternatively provided to be disposed on the second end face according to one embodiment. In this way, the side faces or the lateral faces of the body of the positioning apparatus can continue to remain rotationally symmetric such that the handling of the positioning apparatus continues to be simplified.

In order to ensure that the sterility of a light-guiding fiber is maintained during use with the positioning apparatus according to the invention, provision is made according to a further embodiment for the body of the positioning apparatus, at least in one portion, to consist of a sterilizable material and/or to be coated with a sterilizable material. Here, the channel of the positioning apparatus and the regions of the body of the positioning apparatus adjoining said channel, in particular, are preferably sterilizable. In one configuration of this embodiment, even the entire body of the positioning apparatus may consist of a sterilizable material. Preferably, the sterilizable material is a plastic, in particular polyoxymethylene (POM). Here, this is a cheap sterilizable material, which is easy to process and has the above-described opacity.

In order to simplify the insertion of the light-guiding fiber into the channel of the positioning apparatus, provision is made according to one embodiment for the first end side to have a cutout that tapers in the longitudinal direction of the body and that is centered around the channel, said cutout being embodied to guide the fiber in the direction of the channel. Effectively, this yields a funnel-shaped configuration, and so inserting the light-guiding fiber into the channel is made easier for a user. This is advantageous, in particular, against the background that a fiber facet of a light-guiding fiber should not be brought into contact with other elements of the positioning apparatus where possible, since this would risk damage to the facet, said damage impairing the emission characteristic of the fiber.

In order to ensure simple and cheap production of the positioning apparatus, provision is made according to a further embodiment for the positioning apparatus to be an injection-molded part. Here, in particular, the use of an injection-moldable sterilizable plastic is advantageous.

In a further aspect, the invention relates to a system comprising at least one medical apparatus comprising at least one light source, at least one light-guiding fiber and at least one positioning apparatus as claimed in any one of the preceding claims, wherein the light-guiding fiber is connectable to the light source of the medical apparatus in such a way that at least a portion of laser radiation with a defined radiant flux generated by the light source is coupled into the light-guiding fiber. Further, the medical apparatus comprises a calibration port, wherein the calibration port comprises sensor means that are embodied to ascertain the radiant flux of the laser radiation emerging from the light-guiding fiber, wherein the positioning apparatus can be inserted into the at least one calibration port in such a way that, by way of the subsequent insertion of the at least one light-guiding fiber into the positioning apparatus, the light-guiding fiber is positioned relative to the sensor means in such a way that the radiant flux of the laser radiation emerging from the light-guiding fiber can be ascertained by the sensor means. Here, the calibration port can both be embodied in the medical apparatus and be connected to said medical apparatus as an external appliance.

In a further aspect, the invention relates to a method for calibrating the light source of a system as described above, including the following steps.

Initially, the light-guiding fiber is connected to the light source. Subsequently, the positioning apparatus is inserted into the calibration port and the fiber is inserted into the positioning apparatus and laser radiation with a defined radiant flux is coupled into the light-guiding fiber by way of the light source. The radiant flux of the laser radiation emerging from the light-guiding fiber within the calibration port is then ascertained by means of the sensor means of the calibration port. The ascertained radiant flux emerging from the light-guiding fiber is compared with the radiant flux coupled into the light-guiding fiber, and the radiant flux coupled into the light-guiding fiber is subsequently adapted such that the radiant flux emerging from the light-guiding fiber lies within a defined value range.

BRIEF DESCRIPTION OF THE DRAWINGS

Further features, details and advantages of the invention emerge from the phrasing of the claims and from the following description of exemplary embodiments on the basis of the drawings. In detail:

Below, features that are similar or identical to one another are denoted by the same reference sign.

DETAILED DESCRIPTION OF THE INVENTION

Figure 1:
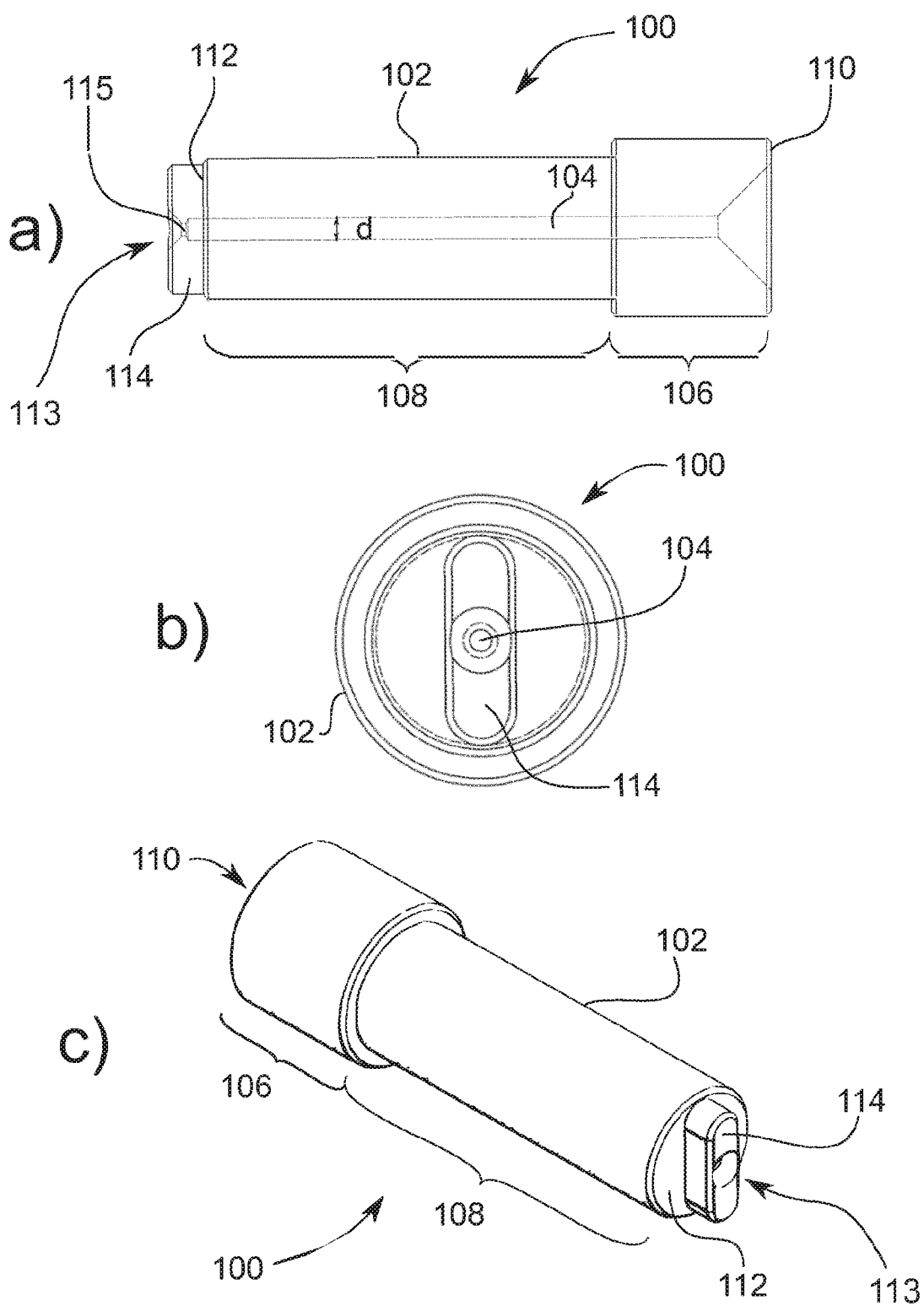
FIG. 1 shows various views of a positioning apparatus for frontally emitting light-guiding fibers.

FIG. 1 shows a schematic illustration of a positioning apparatus 100 for frontally emitting light-guiding fibers. Here, FIG. 1a) shows a lateral view, FIG. 1b) shows a frontal view and FIG. 1c) shows an isometric view of a positioning apparatus 100. Here, the positioning apparatus 100 has a substantially rotationally symmetric body 102, in which a channel 104 for a light-guiding fiber (not illustrated) is formed. Here, the body 102 has a substantially rotationally symmetric embodiment and has two regions 106 and 108, the diameters of which differ. Here, a first region 106 extends from a first end face 110 of the body 102 over approximately one quarter of the overall length of the positioning apparatus 100, while the second region extends from a second end face 112 over the remaining length of the positioning apparatus 100. Here, the edges of the body 102 in the first region 106 and in the second region 108 are beveled by a chamfer in each case such that there are no sharp edges on the positioning apparatus 100.

In the rotationally symmetric configuration of the positioning apparatus 100 as illustrated in FIG. 1, the channel 104 is situated exactly on the axis of rotation of the body 102. Here, the diameter of the channel 104 is adapted in such a way that it is suitable for receiving a light-guiding fiber such that the light-guiding fiber is guided through the channel 104 in the radial direction.

Here, the profile of the channel 104 in the region of the first end face 110 is developed in such a way that, proceeding from a diameter with which a light-guiding fiber inserted into the channel 104 is guided, the diameter of the channel 104 continually increases in the direction of the first end face 110. Effectively, this yields a funnel-shaped configuration of the channel 104 on the side of the first end face 110, said funnel-shaped configuration easing the introduction of a light-guiding fiber into the channel 104.

An alignment element 114 is disposed on the second end face 112. In the illustrated embodiment, the alignment element 114 is an extrusion protruding from the second end face 112, said extrusion having rounded corners. Here, the channel 104 passes through the alignment element 114, as a result of which a frontal cutout 113 is formed in the positioning apparatus, light that has been output coupled frontally from a light-guiding fiber introduced into the channel 104 being able to emerge from the positioning apparatus through said cutout.

In the longitudinal direction, the channel 104 extends as far as into the alignment element 114, with the diameter of the channel 104 being reduced, e.g., halved, approximately half way in the depth of the alignment element 114. This yields an aperture 115 of the channel 104, which, in terms of its diameter, is preferably adapted to the diameter of the core of a light-guiding fiber inserted into the positioning apparatus 100. Proceeding from this reduced diameter, the channel 104 subsequently widens in the longitudinal direction along the alignment element 114, such that the channel 104 has a funnel shape in the region of the frontal cutout 113.

As can easily be identified in FIG. 1a), the transition from the normal diameter d of the channel to the reduced diameter in the region of the alignment element 114 is not sudden; instead, it rather extends over a short transition region in the longitudinal direction of the channel 104. In this way, the cladding of a light-guiding fiber inserted into the positioning apparatus 100 abuts against the material of the alignment element 114 in this transition region while the remaining parts of the light-guiding fiber and, in particular, the light-guiding core of the fiber do not come into contact with the alignment element 114 or, in general, with the body 102 of the positioning apparatus 100. This can avoid damage to the fiber facet of the light-guiding fiber.

Here, the funnel-shaped aperture of the channel 104 in the region of the alignment element 114 ensures that the light output coupled from a light-guiding fiber can emerge in largely unimpeded fashion from the body 102 of the positioning apparatus 100 in the case of a light-guiding fiber that has been inserted into the channel 104 in full. By contrast, if a light-guiding fiber is not introduced into the channel 104 in full, and so the end of the fiber is spaced apart from the tapered region of the channel 104, the body 102 of the positioning apparatus 100 impedes the propagation of the radiation emerging from the light-guiding fiber, and so the radiant flux detected by a calibration port, into which the positioning apparatus 100 has been inserted, drops greatly in relation to the case where the light-guiding fiber has been introduced in full into the channel 104. This allows an incorrect positioning of the light-guiding fiber in the positioning apparatus 100 to be easily identified.

Figure 2:
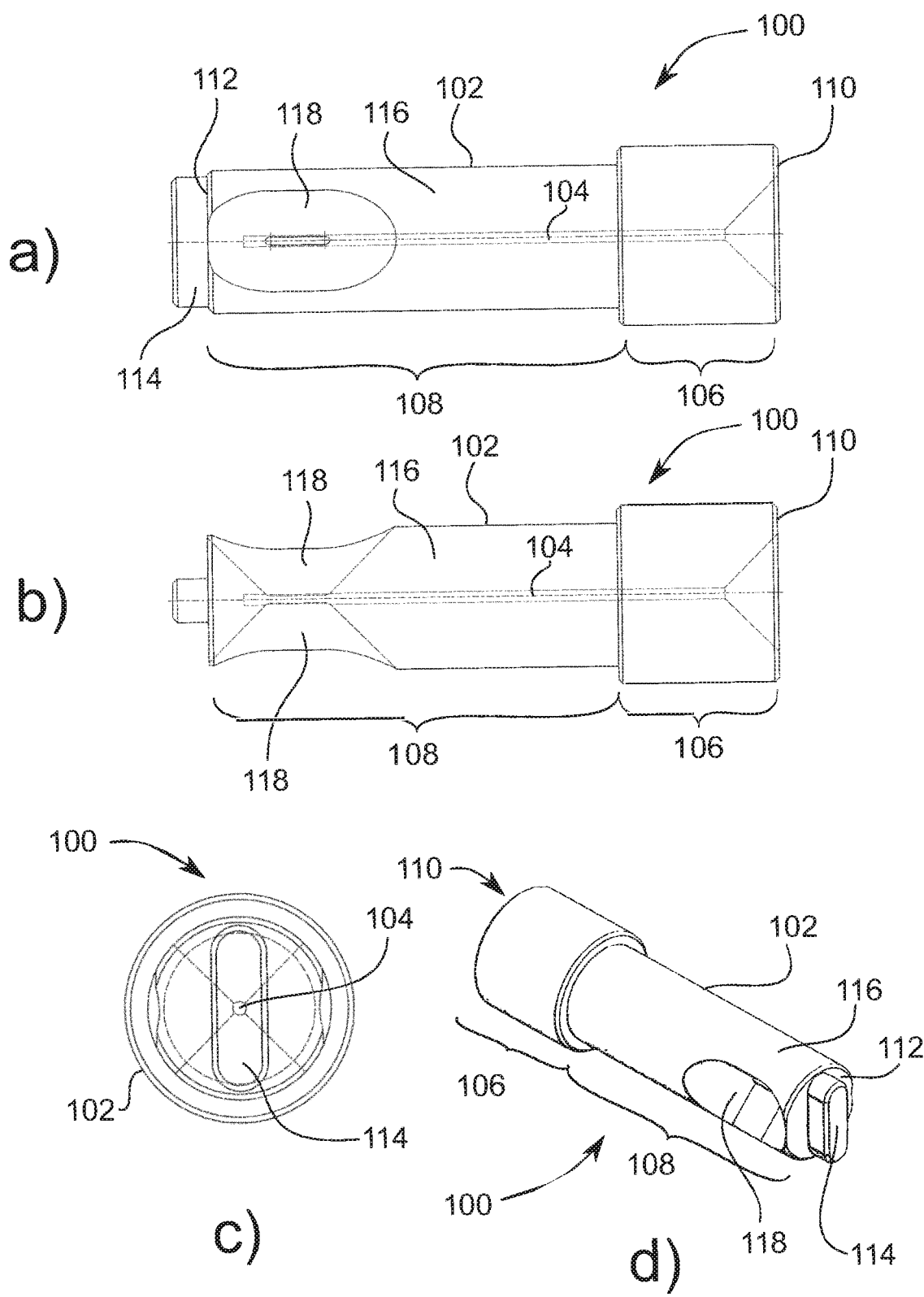
FIG. 2 shows various views of a positioning apparatus for radially emitting light-guiding fibers.

FIG. 2 shows various views of a positioning apparatus 100, which is embodied to receive a light-guiding fiber that output couples the light guided in the light-guiding fiber in the radial direction. Here, the positioning apparatus 100 is shown in a side view in FIG. 2a), in a plan view in FIG. 2b), in a frontal view in FIG. 2c) and in an isometric view in FIG. 2d).

In a manner analogous to the positioning apparatus 100 illustrated in FIG. 1, the positioning apparatus 100 of FIG. 2 also has a substantially rotationally symmetric body 102, which can be subdivided into a first region 106 and a second region 108 that differ in terms of diameter. In a manner likewise analogous to the positioning apparatus 100 of FIG. 1, a channel 104 for receiving a light-guiding fiber is also formed in the positioning apparatus 100 of FIG. 2 along the axis of rotation of the body 102. Here, the channel 104 in the first region 106 is embodied in such a way that the diameter of the channel 104 increases in the direction of a first end face 110 of the body 102. Here, too, the arising funnel shape simplifies the introduction of a light-guiding fiber into the channel 104. In a manner likewise analogous to FIG. 1, an alignment element 114, which is formed as an extrusion on a second end face 112, is formed on the second end face 112 of the body 102.

In contrast to the positioning apparatus 100 illustrated in FIG. 1, the channel 104 of the positioning apparatus 100 illustrated in FIG. 2 has no frontal cutout in the longitudinal direction of the positioning apparatus 100. Instead, lateral cutouts 118 are provided in the lateral face 116 of the second region 108, said lateral cutouts extending from the lateral face 116 to the channel 104 such that a light-guiding fiber disposed in the channel 104 is exposed at its sides. Here, proceeding from the channel 104, the cross section of the lateral cutouts 118 increases in the direction of the lateral face 116 such that a funnel-shaped configuration of the lateral cutouts 118 arises. In this way, laser radiation emitted laterally by a light-guiding fiber introduced into the channel 104 is not impeded in terms of its propagation by the positioning apparatus 100, and so the emission characteristic of a light-guiding fiber disposed in the positioning apparatus 100 can be established well.

Here, the channel 104 extends beyond the lateral cutouts 118 in the longitudinal direction of the body 102 such that a light-guiding fiber introduced into the channel 104 is still guided even behind the lateral cutout 118. This can prevent a light-guiding fiber introduced into the channel 104 from jumping laterally out of the cutouts 118 when introducing it into the channel. Here, a light-guiding fiber jumping out of the lateral cutouts 118 can also be avoided by virtue of the diameter of the lateral cutouts 118 in the circumferential direction of the channel 104 in each case being smaller than the diameter of the light-guiding fiber introduced into the channel 104.

In order to ensure that radiation emerging from a light-guiding fiber introduced into the channel 104 only emerges from the positioning apparatus 100 via the respective cutouts, the body 102 of the positioning apparatus 100 of FIGS. 1 and 2 is produced from an opaque material, such as for example a plastic, in particular polyoxymethylene (POM). Here, an opaque material should be understood to be a material that is not transparent to the light emerging from the fiber such that at least a portion of the light is absorbed or scattered by the material of the body 102 of the positioning apparatus 100. This sets the emission characteristic of the radiation emerging from the positioning apparatus by way of the position and orientation and form of the cutouts 113, 118.

Figure 3:
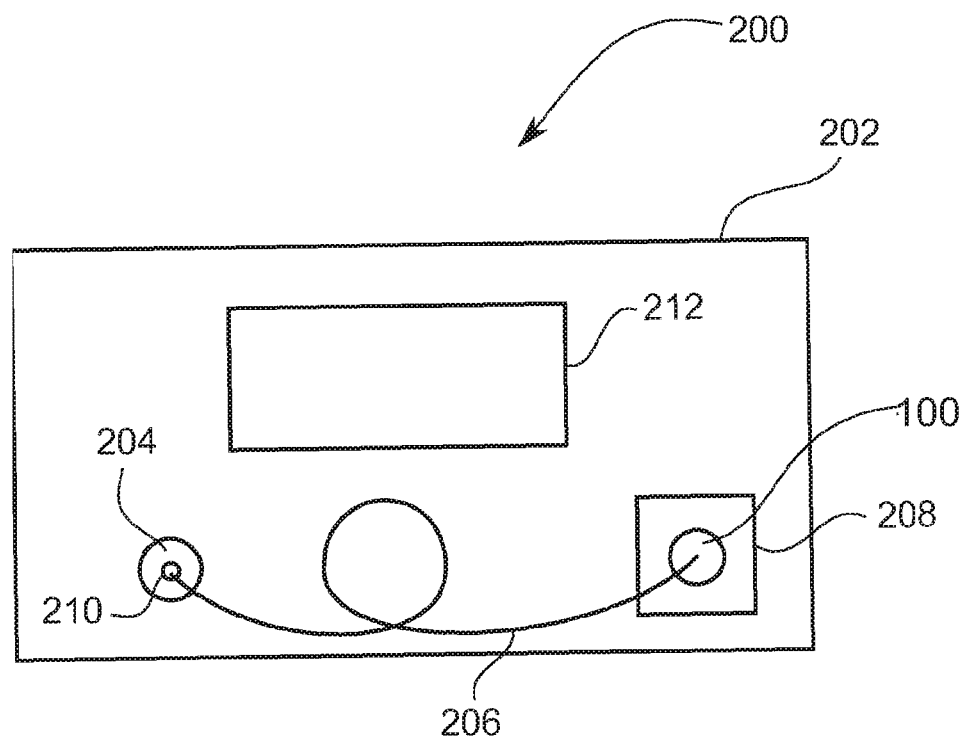
FIG. 3 shows a schematic illustration of a system comprising a medical apparatus and a positioning apparatus.

FIG. 3 shows a schematic illustration of a system 200 comprising a medical apparatus 202, which comprises at least one light source 204 for generating laser radiation having a certain radiant flux and wavelength. By way of example, the light source can be one or more laser diodes. The system 200 further comprises a light-guiding fiber 206 and a calibration port 208, wherein the calibration port 208 is disposed in the medical apparatus 202 in the embodiment illustrated in FIG. 3. However, it would also be possible, by all means, for the calibration port 208 to be embodied as a separate apparatus, which is connected to the medical apparatus 202 by way of at least one data link. Here, the light source 204 of the medical apparatus 202 can be connected via an appropriate optical unit 210 to the light-guiding fiber 206 in such a way that at least a portion of the laser radiation generated by the light source 204 is coupled into the light-guiding fiber 206.

The medical apparatus 202 further comprises an operating element 212, which may be embodied as a touch-sensitive display, for example. By way of this display, it is possible, for example, to set desired output powers, irradiation times and wavelengths of the light source 204 to be emitted. As an alternative to a dedicated selection of output powers, wavelengths and irradiation times, provision can also be made for a user merely to select by way of the operating element 212 a predefined treatment scenario with a reduced selection of further parameters. Then, the medical apparatus 202 is embodied to independently ascertain the corresponding operating parameters of the light source 204 that are necessary for a treatment.

Figure 4:
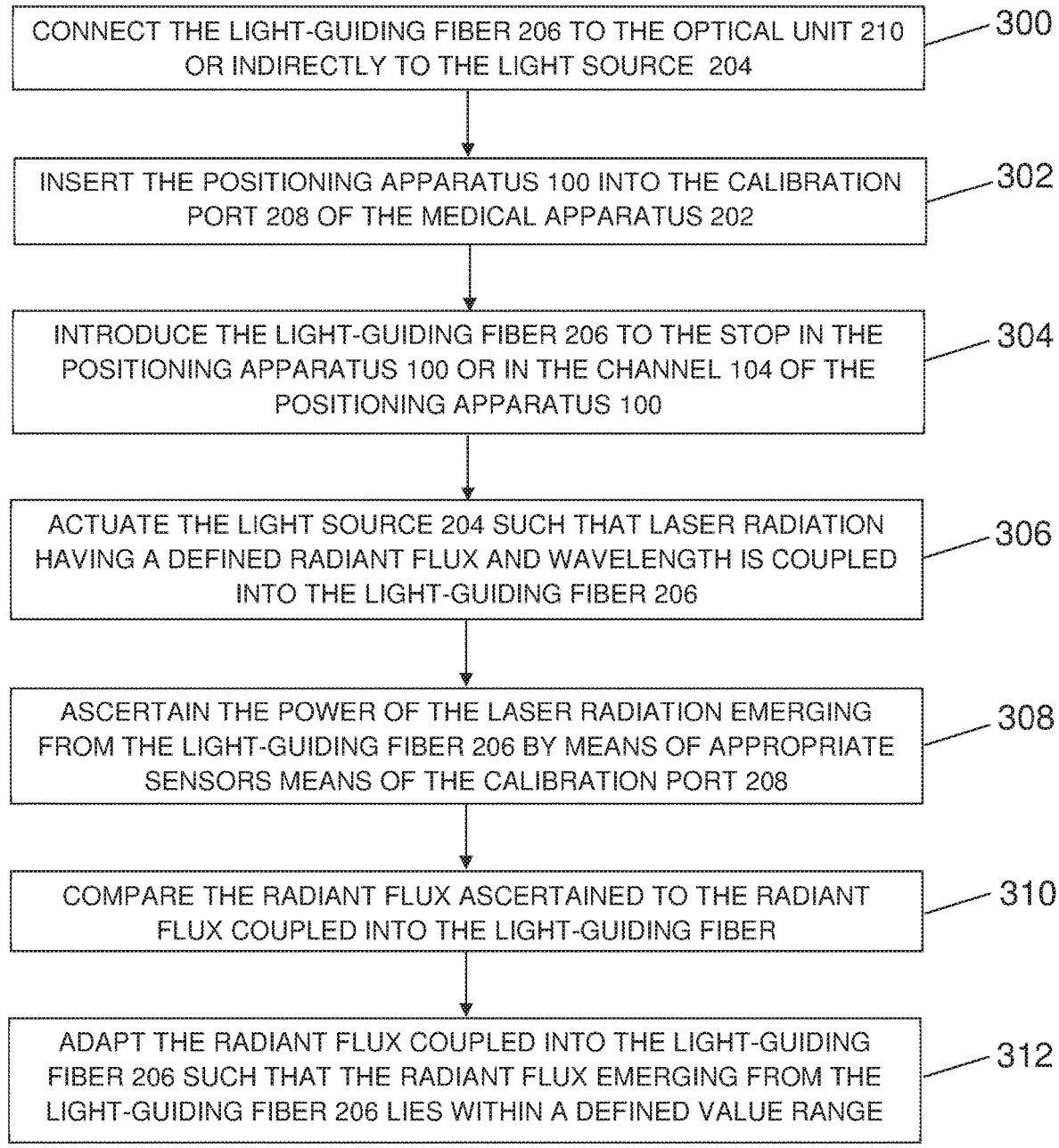
FIG. 4 shows a flowchart of the method according to the invention.

The use of the system 200 is described below with reference to FIG. 4, which illustrates a flowchart of a method according to the invention for use in a positioning apparatus when calibrating a medical system.

In a first method step 300, the light-guiding fiber 206 is initially connected to the optical unit 210 or indirectly connected to the light source 204. By way of example, the optical unit 210 may have an FSMA or FC/PC plug, on which a corresponding mating piece of the light-guiding fiber 206 is screwed, as a result of which it is possible to establish an optical link between light source 204 and light-guiding fiber 206. Subsequently, a positioning apparatus 100, as described above, can be inserted into the calibration port 208 of the medical apparatus 202 in method step 302. Here, the alignment element 114 of the positioning apparatus ensures that the positioning apparatus 100 is correctly aligned in the calibration port 208. Further, at least one microswitch can also be provided in a calibration port 208 for the purposes of detecting the correct alignment and position of the positioning apparatus 100 in the calibration port 208, said microswitch only being actuated in the case of the correct positioning and alignment of the positioning apparatus 100 in the calibration port 208.

Here, an appropriate positioning apparatus 100 must be selected depending on the employed fiber 206, the cutouts of said positioning apparatus being adapted to the emission characteristic of the employed fiber. By way of example, if this relates to a frontally emitting fiber, a positioning apparatus 100 as illustrated in FIG. 1 is necessary, while a positioning apparatus 100 according to FIG. 2 must be used in the case of a light-guiding fiber 206 that emits in the radial direction. Here, the length of the lateral cutout 118 of the positioning apparatus 100 is preferably embodied in such a way that the same positioning apparatus 100 is suitable for different lengths of a radially emitting region of the employed light-guiding fiber 206.

Once the positioning apparatus 100 has been correctly disposed in the calibration port 208, the light-guiding fiber 206 is introduced up to the stop in the positioning apparatus 100 or in the channel 104 of the positioning apparatus 100 in step 304. Subsequently, the light source 204 is actuated in such a way in step 306, for example by the entry of corresponding commands by way of the operating element 212, that laser radiation having a defined radiant flux and wavelength is coupled into the light-guiding fiber 206. By means of appropriate sensors of the calibration port 208, which are not illustrated in FIG. 3, the power of the laser radiation emerging from the light-guiding fiber 206 within the calibration port 208 is ascertained in step 308. The radiant flux thus ascertained is subsequently compared in method step 310 to the radiant flux coupled into the light-guiding fiber, and the radiant flux coupled into the light-guiding fiber 206 is adapted in such a way in method step 312 that the radiant flux emerging from the light-guiding fiber 206 lies within a defined value range. To this end, it is possible either to increase the radiant flux output by the light source 204 or to modify the input coupling of the light power emitted by the light source 204 into the light-guiding fiber 206. Here, the defined value range can be defined, taking account of the emitting area of the light-guiding fiber, in such a way that a defined radiance is emitted by the light-guiding fiber 206 in the case of a certain ascertained radiant flux.

The invention is not restricted to the embodiments explained above but is able to be developed in lots of ways.

By way of example, the form of the positioning apparatus 100 can deviate from the rotationally symmetric form as illustrated in FIGS. 1 and 2. It is by all means possible to embody the positioning apparatus 100 with a rectangular body 102, which is adapted to the geometry of an employed calibration port 208. Further, the illustrated system of FIG. 3 may comprise a medical apparatus 202 that comprises a plurality of light sources 204, which are each coupled to a light-guiding fiber 206. In this way, the flexibility of the treatment options provided by the medical apparatus 202 is increased since a plurality of body regions of a patient to be treated can be irradiated simultaneously.

All features and advantages emerging from the claims, the description and the drawing, including structural details, spatial arrangements and method steps, can be essential to the invention, both on their own and in various combinations.

LIST OF REFERENCE SIGNS

100 Positioning apparatus
102 Body
104 Channel
106 First region
108 Second region
110 First end face
112 Second end face
113 Frontal cutout
114 Alignment element
115 Aperture
116 Lateral face
118 Lateral cutout
200 System
202 Medical apparatus
204 Light source
206 Light-guiding fiber
208 Calibration port
210 Optical unit
212 Operating element

The invention claimed is:

1. A positioning apparatus (100) for positioning a light-guiding fiber (206) in a calibration port (208) of a medical apparatus (202) comprising at least one light source (204) for the light-guiding fiber (206), wherein the positioning apparatus (100) comprises:
an elongate body (102) with two end faces (110, 112) and at least one side face (116), wherein a channel (104) for receiving the light-guiding fiber (206) is formed in the body (102), said channel extending along a longitudinal axis of the body (102) proceeding from a first end face (110), wherein the body (102), at least in one portion, consists of an opaque material in the region of the channel (104) and/or is coated with an opaque material and said body has at least one cutout (113, 118), which extends from a side face (116) and/or the second end face (112) of the body (102) to the channel (104) such that radiation emitted by the light-guiding fiber (206) can only emerge from the positioning apparatus (100) in unimpeded fashion through the at least one cutout (113, 118) wherein the body (102) has at least one elongate, lateral cutout (118), wherein the lateral cutout (118) extends over the length of a part of the channel (104) in the longitudinal direction of the body (102) and extends from the side face (116) of the body (102) to the channel (104) in the radial direction, and wherein the body (102) has at least two elongate, lateral cutouts (118), wherein the lateral cutouts (118) are respectively disposed pair-by-pair on opposite sides of the channel (104).

2. The positioning apparatus (100) as claimed in claim 1, wherein the cross section of the lateral cutout (118) increases from the channel (104) to the side face (116) of the body (102).

3. The positioning apparatus (100) as claimed in claim 1, wherein the channel (104) does not penetrate the second end face (112) of the body (102).

4. The positioning apparatus (100) as claimed in claim 1, wherein the channel (104) extends beyond the length of the lateral cutout (118) in the longitudinal direction of the body (102).

5. The positioning apparatus (100) as claimed in claim 1, wherein the body (102) has a frontal cutout (113) on the second end face (112) of the body (102), wherein the minimum diameter of the frontal cutout (113) is smaller than the diameter of the light-guiding fiber (206).

6. The positioning apparatus (100) as claimed in claim 5, wherein the diameter of the frontal cutout (113) increases in the direction of the second end face (112) of the body (102).

7. The positioning apparatus (100) as claimed in claim 1, wherein the surface of the body (102) is rotationally symmetric about the longitudinal axis of the body (102), wherein the at least one side face of the body (102) is a lateral face (116) of the solid of revolution.

8. The positioning apparatus (100) as claimed in claim 7, wherein the solid of revolution has at least two portions (106, 108) in the longitudinal direction, wherein a first portion (106), which extends from the first end face (110), has a greater radius than the remaining portions (108).

9. The positioning apparatus (100) as claimed in claim 1, wherein the positioning apparatus (100) comprises at least one alignment element (114), the latter being embodied to set the alignment of the positioning apparatus (100) in the calibration port (208).

10. The positioning apparatus (100) as claimed in claim 9, wherein the alignment element (114) is disposed on the second end face (112).

11. The positioning apparatus (100) as claimed in claim 1, wherein the body (102), at least in one portion, consists of a sterilizable plastic and/or is coated with a sterilizable plastic.

12. The positioning apparatus (100) as claimed in claim 11, wherein the sterilizable plastic is polyoxymethylene.

13. The positioning apparatus (100) as claimed in claim 1, wherein the first end side (110) has a cutout that tapers in the longitudinal direction of the body (102) and that is centered around the channel (104), said cutout being embodied to guide the fiber (206) in the direction of the channel (104).

14. The positioning apparatus (100) as claimed in claim 1, wherein the positioning apparatus (100) is an injection-molded part.

15. A system comprising at least one medical apparatus (202) comprising at least one light source (204), at least one light-guiding fiber (206) and at least one positioning apparatus (100) as claimed in claim 1, wherein the light-guiding fiber (206) is connectable to the light source (204) of the medical apparatus (202) so that at least a portion of laser radiation with a defined radiant flux generated by the light source (204) is coupled into the light-guiding fiber (206), wherein the medical apparatus (202) comprises a calibration port (208), wherein the calibration port (208) comprises sensor means that are embodied to ascertain the radiant flux of the laser radiation emerging from the light-guiding fiber (206), wherein the positioning apparatus (100) can be inserted into the at least one calibration port (208) so that, by way of subsequent insertion of the at least one light-guiding fiber (206) into the positioning apparatus (100), the light-guiding fiber (206) is positioned relative to the sensor means so that the radiant flux of the laser radiation emerging from the light-guiding fiber (206) can be ascertained by the sensor means.

16. A method for calibrating the light source (204) of a system as claimed in claim 15, including the following steps:
    connecting the light-guiding fiber (206) to the light source (204), inserting the positioning apparatus (100) into the calibration port (208),
    inserting the light-guiding fiber (206) into the positioning apparatus (100),
    coupling laser radiation with a defined radiant flux into the light-guiding fiber (206) by way of the light source (204),
    ascertaining the radiant flux of the laser radiation emerging from the light- guiding fiber (206) within the calibration port (208) by means of the sensor means of the calibration port (208),
    comparing the ascertained radiant flux emerging from the light-guiding fiber (206) with the radiant flux coupled into the light-guiding fiber (206), and
    adapting the radiant flux coupled into the light-guiding fiber (206) such that the radiant flux emerging from the light-guiding fiber (206) lies within a defined value range.

17. A positioning apparatus (100) for positioning a light-guiding fiber (206) in a calibration port (208) of a medical apparatus (202) comprising at least one light source (204) for the light-guiding fiber (206), wherein the positioning apparatus (100) comprises:
    an elongate body (102) with two end faces (110, 112) and at least one side face (116), wherein a channel (104) for receiving the light-guiding fiber (206) is formed in the body (102), said channel extending along a longitudinal axis of the body (102) proceeding from a first end face (110), wherein the body (102), at least in one portion, consists of an opaque material in the region of the channel (104) and/or is coated with an opaque material and said body has at least one cutout (113, 118), which extends from a side face (116) and/or the second end face (112) of the body (102) to the channel (104) such that radiation emitted by the light-guiding fiber (206) can only emerge from the positioning apparatus (100) in unimpeded fashion through the at least one cutout (113, 118), wherein the body (102) has a frontal cutout (113) on the second end face (112) of the body (102), wherein the minimum diameter of the frontal cutout (113) is smaller than the diameter of the light-guiding fiber (206).

18. The positioning apparatus (100) as claimed in claim 17, wherein the diameter of the frontal cutout (113) increases in the direction of the second end face (112) of the body (102).

19. A positioning apparatus (100) for positioning a light-guiding fiber (206) in a calibration port (208) of a medical apparatus (202) comprising at least one light source (204) for the light-guiding fiber (206), wherein the positioning apparatus (100) comprises:
    an elongate body (102) with two end faces (110, 112) and at least one side face (116), wherein a channel (104) for receiving the light-guiding fiber (206) is formed in the body (102), said channel extending along a longitudinal axis of the body (102) proceeding from a first end face (110), wherein the body (102), at least in one portion, consists of an opaque material in the region of the channel (104) and/or is coated with an opaque material and said body has at least one cutout (113, 118), which extends from a side face (116) and/or the second end face (112) of the body (102) to the channel (104) such that radiation emitted by the light-guiding fiber (206) can only emerge from the positioning apparatus (100) in unimpeded fashion through the at least one cutout (113, 118), wherein the surface of the body (102) is rotationally symmetric about the longitudinal axis of the body (102), wherein the at least one side face of the body (102) is a lateral face (116) of the solid of revolution, and wherein the solid of revolution has at least two portions (106, 108) in the longitudinal direction, wherein a first portion (106), which extends from the first end face (110), has a greater radius than the remaining portions (108).

20. A positioning apparatus (100) for positioning a light-guiding fiber (206) in a calibration port (208) of a medical apparatus (202) comprising at least one light source (204) for the light-guiding fiber (206), wherein the positioning apparatus (100) comprises:
    an elongate body (102) with two end faces (110, 112) and at least one side face (116), wherein a channel (104) for receiving the light-guiding fiber (206) is formed in the body (102), said channel extending along a longitudinal axis of the body (102) proceeding from a first end face (110), wherein the body (102), at least in one portion, consists of an opaque material in the region of the channel (104) and/or is coated with an opaque material and said body has at least one cutout (113, 118), which extends from a side face (116) and/or the second end face (112) of the body (102) to the channel (104) such that radiation emitted by the light-guiding fiber (206) can only emerge from the positioning apparatus (100) in unimpeded fashion through the at least one cutout (113, 118), wherein the first end side (110) has a cutout that tapers in the longitudinal direction of the body (102) and that is centered around the channel (104), said cutout being embodied to guide the fiber (206) in the direction of the channel (104).

* * * * *